US009686745B2

(12) United States Patent
Oleson et al.

(10) Patent No.: US 9,686,745 B2
(45) Date of Patent: Jun. 20, 2017

(54) SYSTEM AND METHOD FOR WIRELESSLY UPLOADING AND DOWNLOADING INFORMATION

(71) Applicant: Under Armour, Inc., Baltimore, MD (US)

(72) Inventors: Mark A. Oleson, Baltimore, MD (US); F. Grant Kovach, Baltimore, MD (US); Nathan Dau, Baltimore, MD (US); Angela Nelligan, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 14/730,620

(22) Filed: Jun. 4, 2015

(65) Prior Publication Data

US 2016/0360487 A1    Dec. 8, 2016

(51) Int. Cl.
*H04B 7/26* (2006.01)
*H04W 52/02* (2009.01)
*H04B 1/3827* (2015.01)
*H04B 1/40* (2015.01)
*A43B 3/00* (2006.01)

(52) U.S. Cl.
CPC ....... *H04W 52/0254* (2013.01); *A43B 3/0005* (2013.01); *H04B 1/385* (2013.01); *H04B 1/40* (2013.01); *H04B 7/26* (2013.01); *H04W 52/0229* (2013.01); *Y02B 60/50* (2013.01)

(58) Field of Classification Search
CPC ................................................. H04M 1/7253
See application file for complete search history.

(56) References Cited

U.S. PATENT DOCUMENTS

| 7,299,034 B2 * | 11/2007 | Kates | H04M 1/05 455/415 |
|---|---|---|---|
| 2010/0185398 A1 * | 7/2010 | Berns | A41D 13/1281 702/19 |
| 2014/0095901 A1 * | 4/2014 | Stefanov | G06F 1/3206 713/310 |
| 2016/0026977 A1 * | 1/2016 | Umapathy | G06Q 10/1093 705/7.18 |
| 2016/0100439 A1 * | 4/2016 | Oleson | H04W 76/021 455/41.1 |
| 2016/0345269 A1 * | 11/2016 | Basehore | H04W 52/0254 |

* cited by examiner

*Primary Examiner* — David Bilodeau

(57) ABSTRACT

A device for use with a wireless transceiver that is operable to transmit a data file. The device includes a communication component, a processing component, a parameter detecting component and a controlling component. The communication component wirelessly communicates with the transceiver. The processing component operates in a first manner. The parameter detecting component detects a first parameter and generates a parameter signal based on the detected first parameter. The controlling component generates a wake-up signal based on the parameter signal. The communication component can further receive the data file based on the wake-up signal. The processing component can further operate in a second manner based on the data file.

20 Claims, 9 Drawing Sheets

SYSTEM AND METHOD FOR WIRELESSLY UPLOADING AND DOWNLOADING INFORMATION

BACKGROUND

The present invention generally deals with systems and methods for wirelessly uploading and downloading information.

There exists a need for a system and method that allows the wireless device to sit idle until the device receives a signal to wake-up.

BRIEF SUMMARY OF THE DRAWINGS

The accompanying drawings, which are incorporated in and form a part of the specification, illustrate an exemplary embodiment of the present invention and, together with the description, serve to explain the principles of the invention. In the drawings.

SUMMARY

The present invention is drawn to a system and method that can prevent electronic devices from actively searching or receiving signals when not in-use.

Various embodiments described herein are drawn to a device for use with a wireless transceiver that is operable to transmit a data file. The device includes a communication component, a processing component, a parameter detecting component and a controlling component. The communication component wirelessly communicates with the transceiver. The processing component operates in a first manner. The parameter detecting component detects a first parameter and generates a parameter signal based on the detected first parameter. The controlling component generates a wake-up signal based on the parameter signal. The communication component can further receive the data file based on the wake-up signal. The processing component can further operate in a second manner based on the data file.

EXAMPLE EMBODIMENTS

In today's market, one of the most commonly sought after characteristic of wireless electronic devices is a long lasting battery. An example is a cellphone with the capability to search the web, play video games, or receive phone updates. While the user's phone is connected to their home network, they can quickly access the web, download updates, etc. However, if the user walks leaves their router's transmitting range, the phone will automatically continue to search for a new network. Therefore, the phone continues to stay "in-use" while searching for a connection, using up a large amount of the battery. A cellphone is one of the many wireless devices that are comprised of electronic components operable to transmit and receive data. A conventional wireless device will now be described with reference to FIG. 1.

Figure 1:
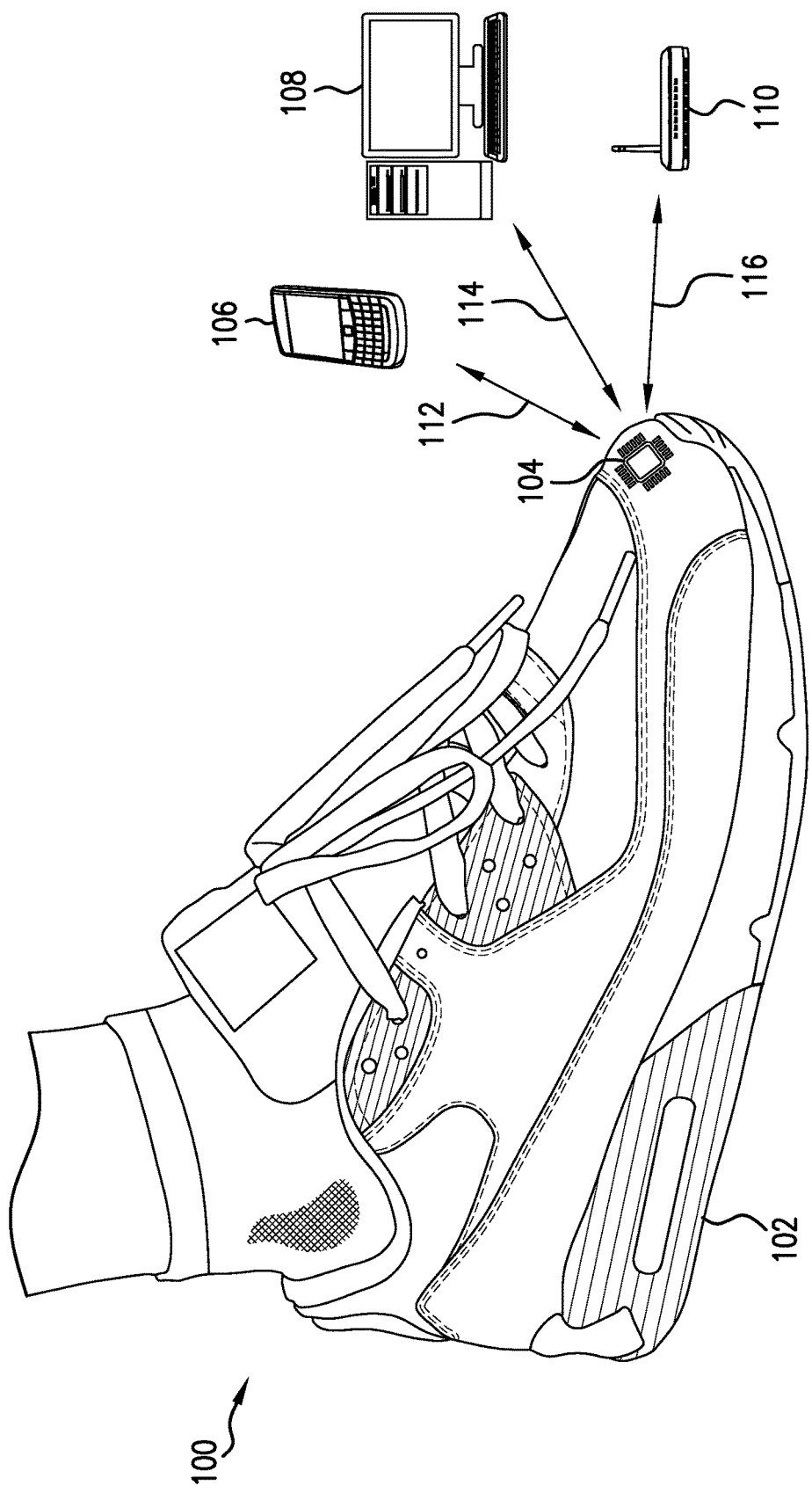
FIG. 1 illustrates a conventional system capable of wirelessly transmitting and receiving signals.

FIG. 1 illustrates a conventional system 100 capable of wirelessly transmitting and receiving signals.

As shown in the figure, system 100 includes a shoe 102 and a wireless device 104, disposed in shoe 102.

Wireless device 104 is able to wirelessly transmit and receive data, perform processing and store data. For example, system 100 may be a "smart" shoe wherein wireless device 104 is able to perform functions, such as monitor distance traveled, estimate calories burned, etc., while a person is using shoe 102.

Wireless device 104 may be able to transmit or receive data from other wireless devices, such as a cell phone 106 as shown by arrow 112, a computer 108 as shown by arrow 114 and a wireless router 110 as shown by arrow 116. For example, if wireless device 104 has updated data from use by a user, e.g., an amount of calories burned from a latest running session, wireless device 104 may be programmed to "upload the data," or transmit the data, to another wireless device, e.g., computer 108. Further, there may be cases where the operation of wireless device 104 may be altered with a software update that may be "downloaded," or received from another wireless device, e.g., computer 108.

When transmitting data to (or receiving data from) one of cell phone 106, computer 108 or wireless router 110, typically there must be some sort of handshake, wherein the targeted receiver (or transmitter) is sought and identified, and then communication protocols are exchanged between the targeted receiver (or transmitter) and wireless device 104.

This searching, identifying and exchange of protocols may expend much power from wireless device 104. As such, wireless device 104 includes a power source, which may or may not be rechargeable. All of the functions of wireless device 104 consume power. However, if a particular targeted receiver is not in range of wireless device 104, wireless device 104 may nevertheless expend a large portion of its valuable power searching for the non-existent receiver.

More particularly, a large problem with the system FIG. 1 is wireless device 104 attempting to transmit data when shoe 102 is not in use. In this example, shoe 102 could be sitting in a closet, in a shoe box, or even sitting in a factory waiting to be assembled. While sitting, in some cases device 104 may continue to search for a local network and any possible updates. If an update is wirelessly transmitted, device 104 will search for the update and download it. If no update is available to download, device 104 may continue to upload any stored data to the user's cellphone 106 or computer 108. This process can occur multiple times while the shoe 102 is not in use. This leads to an unacceptable loss of power.

The present invention is drawn to a wearable device that is capable of communicating wirelessly with a wireless transceiver. The wearable device is capable of internally generating a wake-up signal, based on a detected parameter.

Waking up the wearable device with the wake-up signal decreases the likelihood that the device will attempt to upload or download data at an inappropriate time or place. Non-limiting example embodiments of wearable devices in accordance with aspects of the present invention include a shoe, wristwatch, bracelet, clothing, etc.

For example, for purposes of discussion, consider an example embodiment of a shoe having a functional device therein, wherein the functional device is able to perform functions and wirelessly upload and download data. Further, consider the situation where the shoe is sitting in a shoe box or in a user's closet. In accordance with aspects of the present invention, the functional device in the shoe will remain idle, or inactive. In order to "wake up" or turn on, the functional device may detect at least one detectable parameter, non-limiting examples of which include pressure on the sole or tongue of the shoe, acceleration, and change in position. Once the detectable parameters are detected, the functional device will wake up, wherein it may start to download or upload data as appropriate. If an update is broadcasted over the air, the functional device, now active, would download the update. Similarly, in some embodiments, if the device has stored data from the user's exercise session user has been walking or running for several minutes or hours, the device may upload the user's performance data.

Aspects of the present invention are drawn to a system and method.

Aspects of the present invention will now be described with reference to FIGS. 2-8.

Figure 2:
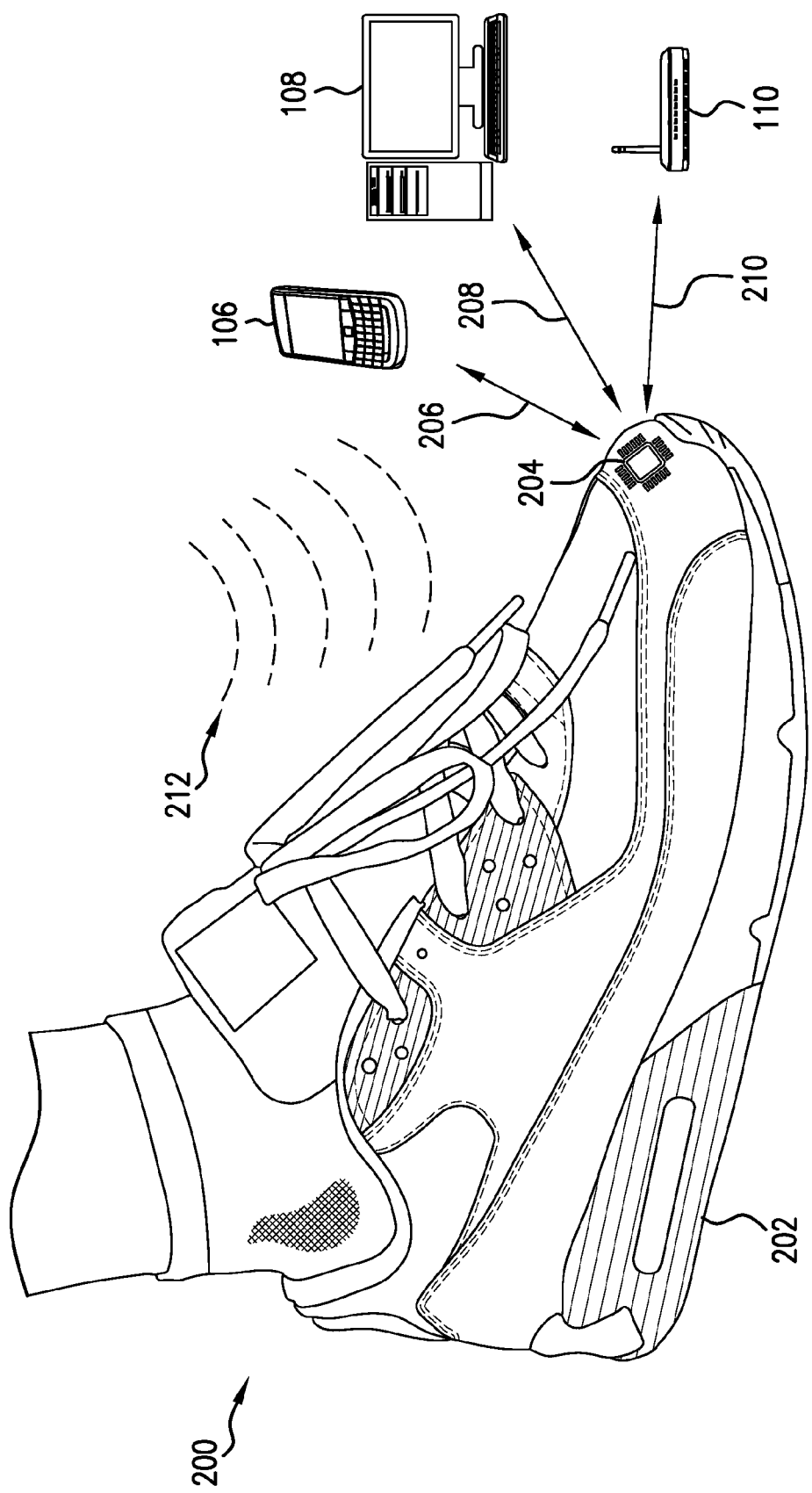
FIG. 2 illustrates a system in accordance with aspects of the present invention, which is capable of wirelessly transmitting and receiving signals.

FIG. 2 illustrates a system 200 in accordance with aspects of the present invention, which is capable of wirelessly transmitting and receiving signals.

As shown in the figure, system 200 includes a shoe 202 and a wireless device 204, disposed in shoe 202.

Wireless device 204 is able to wirelessly transmit and receive data, perform processing and store data. For example, system 200 may be a "smart" shoe wherein wireless device 204 is able to perform functions, such as monitor distance traveled, estimate calories burned, etc., while a person is using shoe 202.

Wireless device 204 may be able to transmit or receive data from other wireless devices, such as cell phone 106 as shown by arrow 206, computer 108 as shown by arrow 208 and wireless router 110 as shown by arrow 210. Wireless device 204 differs from wireless device 104 of system 100 as discussed above with reference to FIG. 1, in that wireless device 204 is additionally able to detect a parameter. In this example, the parameter is a GPS signal 212. Further, wireless device 204 will transmit or receive data from other wireless devices based on the detected parameter, which in this example is GPS signal 212.

For example, if wireless device 204 has updated data from use by a user, e.g., an amount of calories burned from a latest running session, wireless device 104 may be programmed to upload the data to another wireless device, e.g., computer 108, when wireless device 204 receives GPS signal 212. Further, there may be cases where the operation of wireless device 204 may be altered with a software update that may be downloaded from another wireless device, e.g., computer 108, when wireless device 204 receives GPS signal 212.

Wireless device 204 addresses the large problem with the system FIG. 1. In particular, by detecting a predetermined parameter associated with use of shoe 202, wireless device 204 will be less likely to attempt to transmit data when shoe 202 is not in use. For example, shoe 202 could be sitting in a closet, in a shoe box, or even sitting in a factory waiting to be assembled. For purposes of discussion, let the predetermined parameter to be detected that is associated with use of shoe 202 be pressure on the sole—thus indicating that a user is standing with shoe 202. This aspect of the present invention would eliminate the ability for device 204 to continue to search for a local network and any possible updates, for example when shoe 202 is not in use. If an update is wirelessly available, device 204 will search for the update and download it at the appropriate time and place based on the detection of a parameter. Further, device 204 may upload any stored data to the user's cellphone 106 or computer 108 at the appropriate time and place based on the detection of a parameter. This leads to power savings.

An example device 204 in accordance with aspects of the present invention will now be described with reference to FIG. 3.

As shown in the figure, device 204 includes a communication component 302, a processing component 304, a parameter detecting component 306 and a controlling component 308.

In this example, communication component 302, processing component 304, parameter detecting component 306 and controlling component 308 are illustrated as individual devices. However, in some embodiments, at least two of communication component 302, processing component 304, parameter detecting component 306 and controlling component 308 may be combined as a unitary device. Further, in some embodiments, at least one of communication component 302, processing component 304, parameter detecting component 306 and controlling component 308 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

In this embodiment, communication component 302 is able to receive a received signal 310 and to output received data 314, based on received signal 310, to processing component 304 via a communication channel 316. Additionally, communication component 302 is able to receive transmitted data 318 from processing component 304 via a communication channel 320. Parameter detecting component 306 is able to receive a parameter signal 322 and to output detected parameter data 324, based on parameter signal 322, to controlling component 308 via a communication channel 326. Controlling component 308 is able to output: a communication control signal 328 to communication component 302 via a communication channel 330; a detector control signal 332 to parameter detecting component 306 via a communication channel 334; and a processing control signal 336 to processing component 304 via a communication channel 338.

Communication component 302 may be any system or device that is able to transmit and/or receive data in a known manner. Non-limiting examples of communication component 302 include a circuit that is able to transmit and/or receive data via one of the group consisting of Bluetooth, Bluetooth Low Energy, IEEE 802.11, ZigBee, 4G LTE, 3G, ANT, ANT+ and Wind, bit banging.

Processing component 304 may be any system or device that is able to perform operations. In some embodiments processing component may additionally be any system or device that is able to generate transmitted data 318.

Parameter detecting component 306 may be any system or device that is able to detect predetermined parameters. Non-limiting examples of parameter detecting component 306 include a circuit that is able to detect one the group selected from sound, a change in sound, proximity, change in proximity, location, a change in location, position, velocity, acceleration, jerk, a change in jerk, temperature, a change in temperature, impedance, a change in impedance, resistance, a change in resistance, capacitance, a change in capacitance, inductance, a change in inductance, pressure, a change in pressure, magnetic field, a change in magnetic field, electric field, a change in electric field, an electromagnetic signal, a change in an electromagnetic signal, time, a change in time, a radio advertisement and combinations thereof.

Controlling component 308 may be any system or device that is able to control operation of communication component 302, processing component 304 and parameter detecting component 306.

Communication channels 316, 320, 324, 330, 334 and 338 may be wired or wireless communication channels that are able to carry information in the form of data and/or signals.

Figure 4:
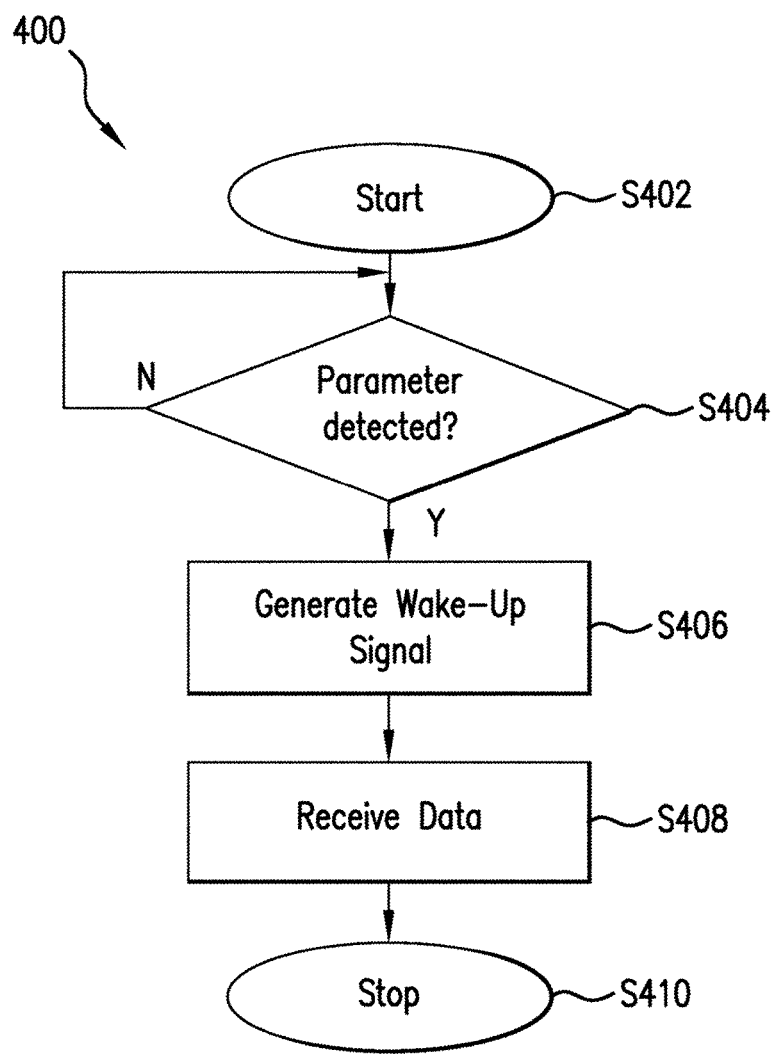
FIG. 4 illustrates a method of downloading a data file in accordance with aspect of the present invention.
Figure 5:
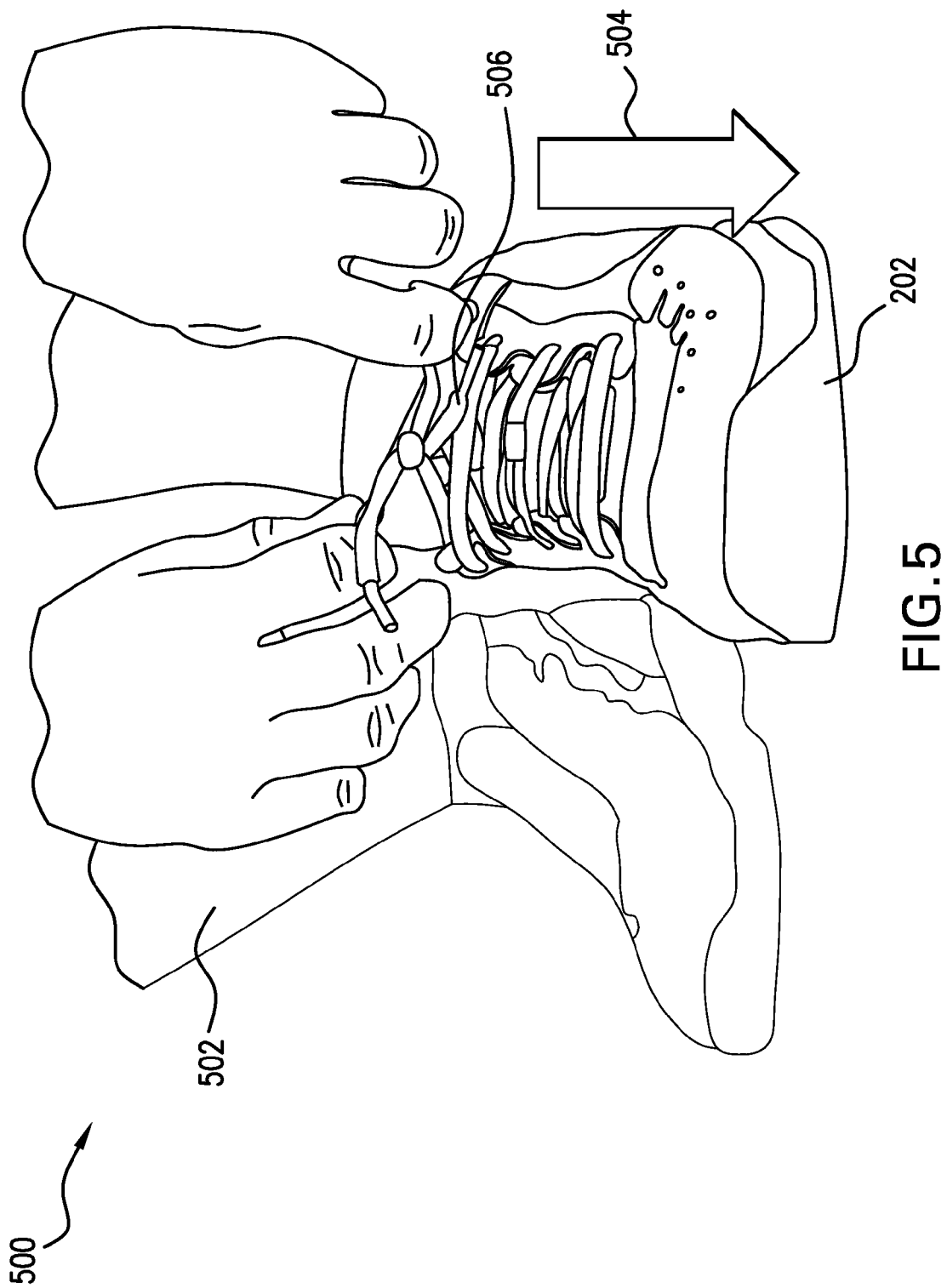
FIG. 5 illustrates an example of a detecting parameters with a wireless device in accordance with aspects of the present invention.
Figure 6:
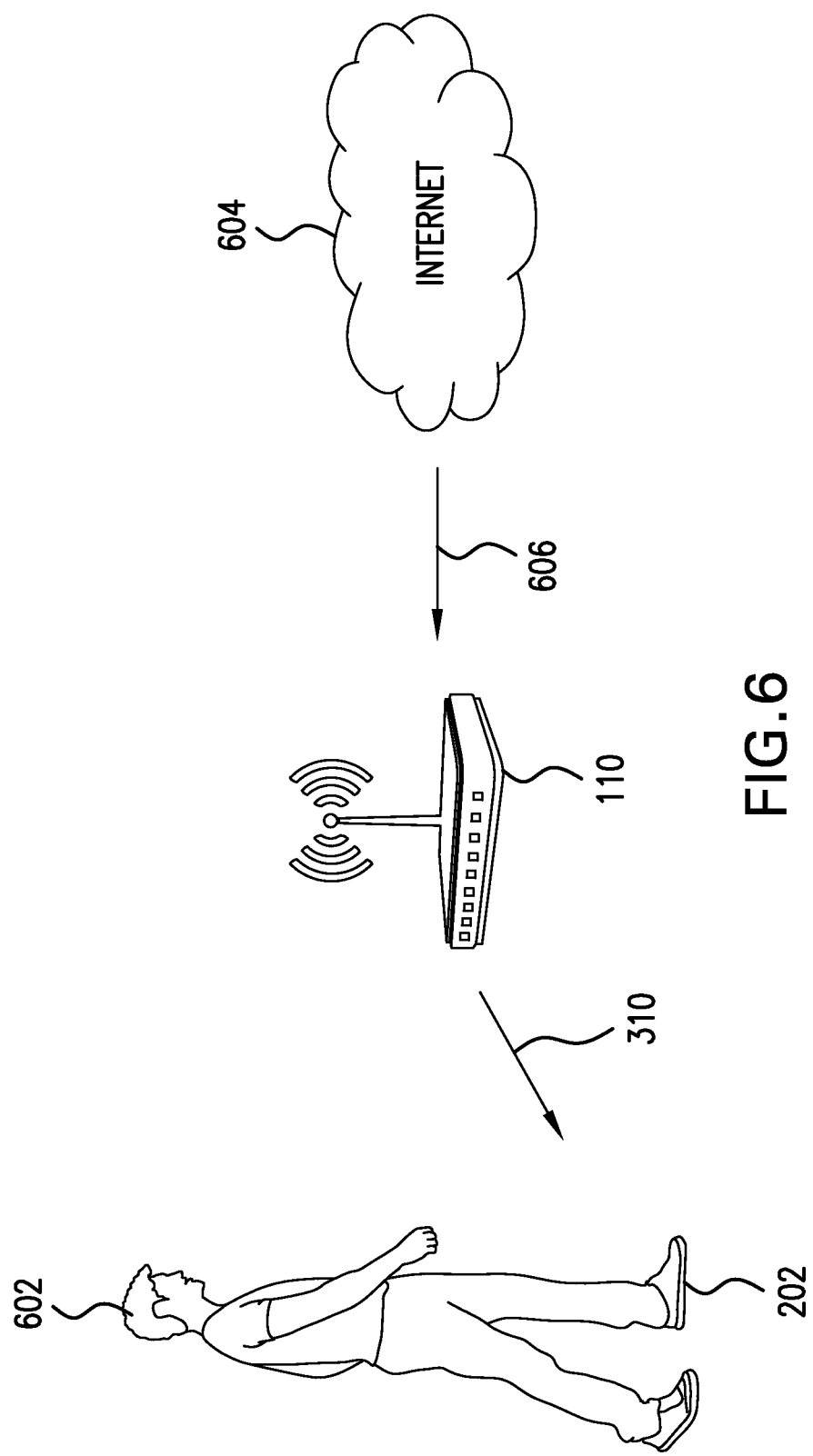
FIG. 6 illustrates an example embodiment of downloading data with a wireless device in accordance with aspects of the present invention.

An example method of downloading data in accordance with aspect of the present invention will now be further described with additional reference to FIG. 4-6.

FIG. 4 illustrates a method 400 of downloading data in accordance with aspect of the present invention.

As shown in the figure, method 400 starts (S402) and it is determined whether a parameter is detected (S404). For example, returning to FIG. 2, let wireless device 204 be able to detect GPS signal 212 as the detectable parameter. As shown in FIG. 3, parameter signal 322, in this example, therefore would be GPS signal 212. Further, in this example embodiment, GPS signal 212 corresponds to a GPS signal indicating a geodetic position of the home of a user of shoe 202. As such, GPS signal 212 would only be detected by parameter detecting component 306 when the user of shoe 202 is at home. Therefore, it at home, parameter detecting component 306 would detect parameter signal 322 and output detected parameter data 324. Further, when not at home, parameter detecting component 306 would not detect parameter signal 322 and would therefore not output detected parameter data 324.

In some embodiments, detected parameter data 324 is parameter signal 322. In other embodiments, detected parameter data 324 corresponds to parameter signal 322.

Another example of a parameter being detected will now be further described with reference to FIG. 5.

FIG. 5 illustrates an example of detecting parameters via a shoe in accordance with aspects of the present invention. The figure includes a user 502 wearing shoe 202, an arrow 504 indicating a first detected parameter, and a shoelace 506 having a second detected parameter associated therewith. In this example, one detectable parameter as associated with arrow 504 is downward pressure. As shown in FIG. 3, this parameter may be detected by parameter detecting component 306 when user 502 puts on shoe 202 and pressure is exerted in a direction of arrow 504 onto the sole of shoe 202. Another detectable parameter is associated with pressure at shoelace 506. As shown in FIG. 3, this parameter may be detected by parameter detecting component 306 when user 502 ties shoelace 506 and pressure is exerted onto the tongue of shoe 102.

It should be noted that a Wi-Fi broadcast is not a parameter to be detected in accordance with aspects of the present invention. For example, some conventional memory chips for digital cameras include Wi-Fi capability, wherein upon detection of a Wi-Fi broadcast the conventional memory chips will upload its stored data to the broadcasting Wi-Fi network. Such chips would have the same problem as the conventional system discussed above with reference to FIG. 1. In particular, such Wi-Fi enabled memory chips would constantly search for a Wi-Fi broadcast from a Wi-Fi network, thus waist much valuable power.

In some embodiments a single parameter may be detected, whereas in other embodiments, multiple parameters may be detected. Detecting multiple parameters will increase the likelihood that controlling component 308 will not generate a "wake-up" signal to communication component 302 at an improper time and place. For example, if only a GPS signal indicating a geodetic position of the home of the user of shoe 202 were the detectable parameter, but the shoe was stored in a closet, such a time might not be proper to generate a "wake-up" signal to communication component 302. Similarly, if only pressure were the detectable parameter, but the user was walking in the shoe at the gym, such a place might not be proper to generate a "wake-up" signal to communication component 302. As such, in some example a GPS signal indicating a geodetic position of the home of a user of shoe 202 may be a first detectable parameter and pressure may be a second detectable parameter. In this manner, when the user is at home and wearing shoe 202, it would be proper to generate a "wake-up" signal to communication component 302.

Returning to FIG. 4, if a parameter is not detected (N at S404), method 400 waits until one is detected (return to S404). If a parameter is detected (Y at S404), then a wake-up signal is generated (S406). For example, returning to FIG. 3, controlling component 308 instructs, via detector control signal 332, parameter detecting component 306 to provide detected parameter data 324 to controlling component 308. Processing component 304 receiving detected parameter data 324 indicates that a parameter has been detected. Controlling component 308 provides a "wake-up" signal to communication component 302 as communication control signal 328. This wake-up signal instructs communication component 302 to receive received signal 310.

Returning to FIG. 4, now that a wake-up signal is generated (S406), data is received (S408). For example, returning to FIG. 3, communication control signal 328 instructs communication component 302 to receive received signal 310.

Method 400 then stops (S410).

Method 400 describes downloading data in accordance with aspects of the present invention. In an example embodiment the downloaded data is a firmware update. This will be further described with reference to FIG. 6.

FIG. 6 illustrates an example embodiment of wirelessly downloading data in accordance with aspects of the present invention.

As shown, FIG. 6 includes a user 602 having shoe 202, wireless router 110 and the internet 604. Internet 604 is operable to output the firmware update as a data file to wireless router 110 by way of channel 606. Wireless router 110 is operable to output received signal 310 as the firmware update (as a data file) to shoe 202.

Internet 604 is a global system of interconnected computer networks that link several billion devices worldwide. The internet consists of networks linked by a broad array of electronic, wireless, and optical networking technologies. The Internet carries an extensive range of information resources for file sharing.

Wireless router 110 is a device that performs the functions of a router but also includes the functions of a wireless access point. Wireless router 110 is used to provide access to the Internet or a private computer network.

Figure 3:
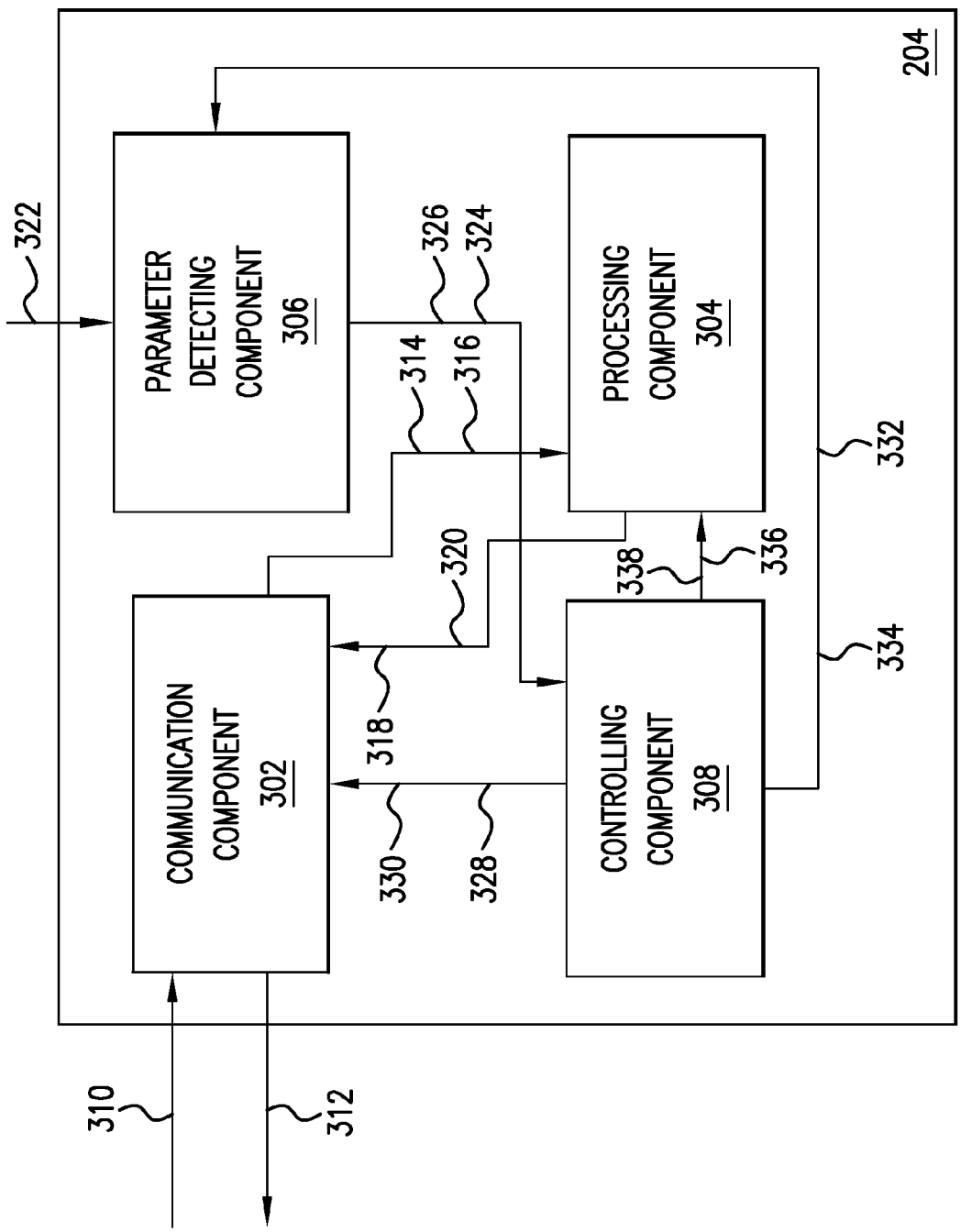
FIG. 3 illustrates a wireless device from the system of FIG. 2, in accordance with aspects of the present invention.

For example, with additional reference to FIG. 3, let processing component 304 of wireless device 204 of shoe 202 be a programmable circuit that is operating in a first manner, e.g., in accordance with original instructions disposed therein, when wireless device 200 is manufactured, i.e., the factory settings. Now, suppose that the firmware update is available that will enable processing component 304 to operate in a second, more efficient manner. Wireless device 200 will need to obtain the firmware update, such as by downloading from a data source.

Returning to FIG. 6, let wireless router 110 have the firmware update in the form of a data file. In order for wireless device 204 to obtain the firmware update from wireless router 110, wireless device 200 must know to "ask" wireless router 110 for any updates.

As mentioned above with reference to FIG. 1, when wireless device 104 is constantly searching for wireless router 110 much power may be lost. For example, if shoe 102 is not located sufficiently close to wireless router 110 so as to complete a handshake and subsequently download data, than searching for wireless router 110 would waste power.

As such, in accordance with aspects of the present invention, returning to FIG. 3, communication component 302 will not be woken up to search for and receive data, which in this example is a firmware update for processing component 304, unless another predetermined parameter is detected by parameter detecting component 306. This second detected parameter increases the likelihood that communication component 302 will only search for and download data when wireless device 204 is in a time and location at which downloadable data is available.

Therefore, in this example, when parameter detecting component 306 receives the correct GPS signal as parameter signal 322, communication component 302 is ultimately able to search for and download the firmware update as received signal 310. Controlling component 308 then instructs, via communication control signal 328, communication component 302 to provide received data 314 to processing component 304. In this manner, the firmware update is passed to processing component 304 as received data 314. Processing component 304 is then reprogrammed by the firmware update so that processing component 304 may operate in a new, more efficient manner.

As shown in FIG. 6, when user 602 is sufficiently close to wireless router 110, shoe 202 will wake up to search for and receive the firmware update.

The above discussed embodiment deals with downloading data. However, aspects of the present invention additionally apply to uploading data.

An example embodiment of uploading data in accordance with aspects of the present invention will now be further described with reference to FIGS. 7-8.

Figure 7:
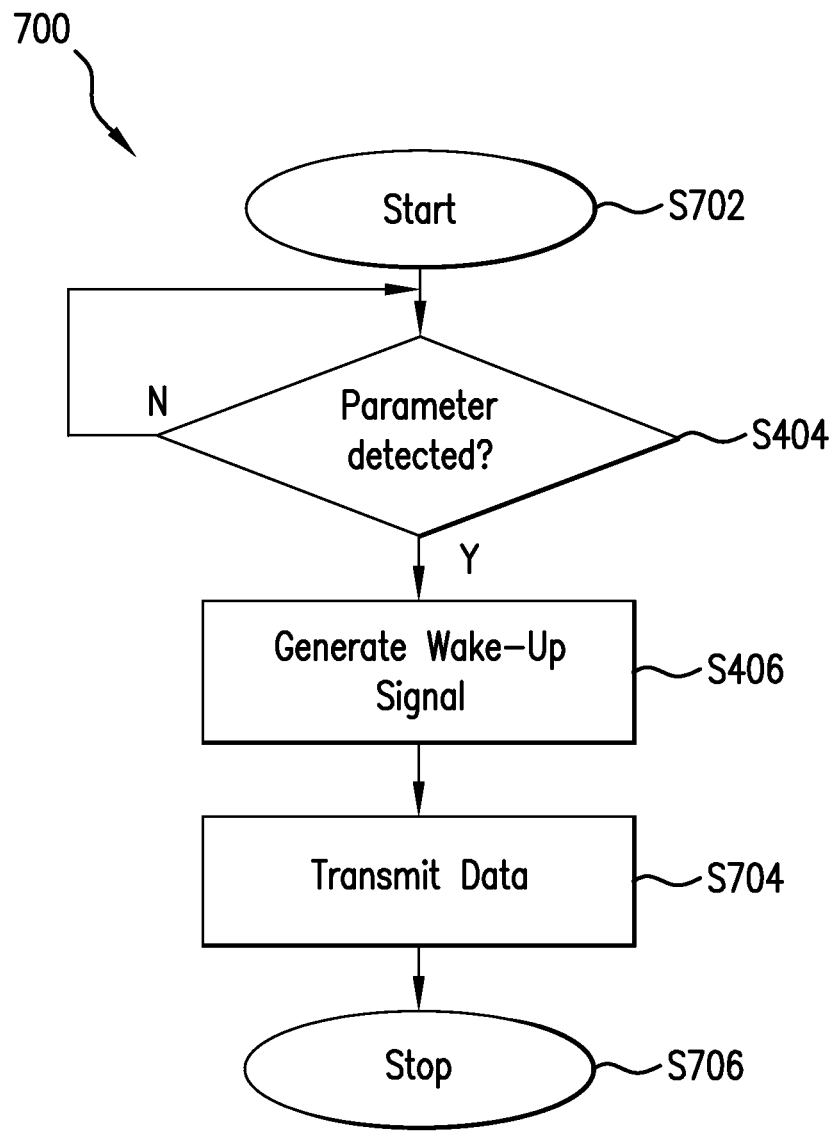
FIG. 7 illustrates a method of uploading data with a wireless device in accordance with aspect of the present invention.

FIG. 7 illustrates a method 700 of uploading a data file in accordance with aspect of the present invention.

As shown in the figure, method 700 starts (S702) and it is determined whether a parameter is detected (S404). This is similar that that discussed above with reference to FIG. 4.

Returning to FIG. 7, again if a parameter is not detected (N at S404), method 400 waits until one is detected (return to S404). Further, if a parameter is detected (Y at S404), then a wake-up signal is generated (S406). Again, this is similar to that as discussed with reference to FIG. 4.

Now that a wake-up signal is generated (S406), data is transmitted (S407). For example, returning to FIG. 3, let processing component 304 have data stored therein, wherein the data may include data associated with an exercise session, e.g., miles walked, calories burned, etc. This example will be further described with reference to FIG. 8.

Figure 8:
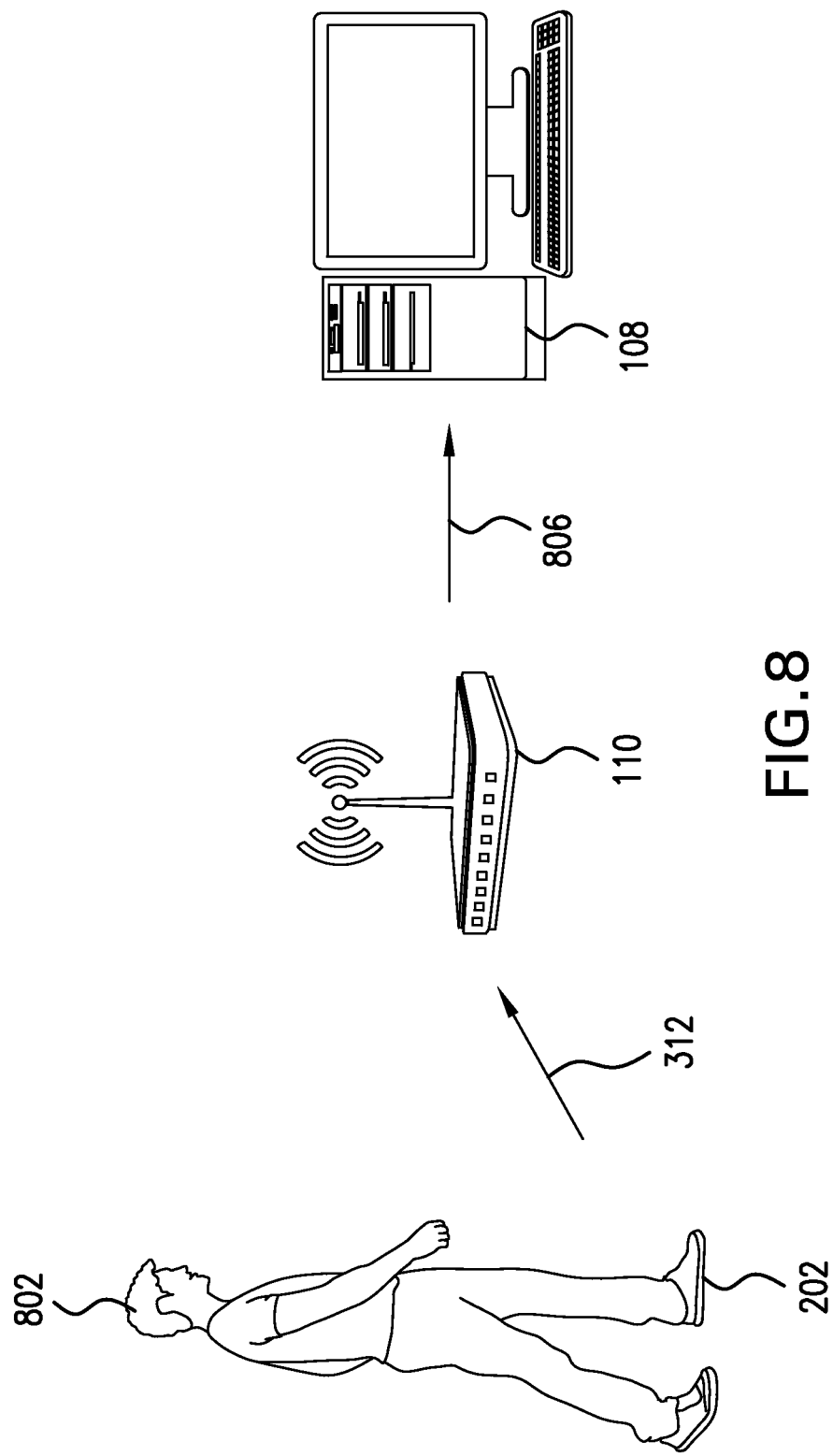
FIG. 8 illustrates an example embodiment of uploading data with a wireless device in accordance with aspects of the present invention.

FIG. 8 illustrates an example embodiment of wirelessly downloading data in accordance with aspects of the present invention.

As shown, FIG. 8 includes a user 802 having shoe 202, wireless router 110 and computer 108. In this example, shoe 202 is operable to output transmitted signal 312 to wireless router 110, which in turn will transmit the transmitted signal 312 to computer 108.

For example, with additional reference to FIG. 3, as mentioned earlier, let processing component 304 have data stored therein, wherein the data may include data associated with an exercise session, e.g., miles walked, calories burned, etc. Now, wireless device 204 is programmed to upload information stored in processing component to computer 108. Wireless device 200 will need to search for and communicate with computer 108.

Returning to FIG. 8, let processing component 304 (in wireless device 204 in shoe 202) have data stored therein, which is to be uploaded to computer 108. In order for wireless device 204 to upload the data, wireless device 200 must know to find access to computer, which in this case includes through wireless router 110.

In accordance with aspects of the present invention, returning to FIG. 3, communication component 302 will not be woken up to search for computer 108 in order to upload data, which in this example includes exercise session data, unless another predetermined parameter is detected by parameter detecting component 306. This second detected parameter increases the likelihood that communication component 302 will only upload data when wireless device 204 is in a time and location at which uploading data is viable.

Therefore, in this example, when parameter detecting component 306 receives the correct GPS signal as parameter signal 322, communication component 302 is ultimately able to search for computer 108, which in this case includes searching for wireless router 110, and to upload the exercise data, which in this case is transmitted data 316 from processing component 304. The exercise data is then transmitted from communication component 302 as transmitted signal 312. In this situation, transmitted signal 312 may be called an upload signal, as data is uploaded from shoe 202 to wireless router 110. Wireless router 110 then transmits the exercise data along a channel 806 to computer 108.

As shown in FIG. 8, when user 802 is sufficiently close to wireless router 110, shoe 202 will wake up to search for computer 108 and upload the exercise data.

Returning to FIG. 7, method 700 then stops (S706).

Another example embodiment of downloading data to a wireless device, or uploading data to a wireless device in accordance with aspects of the present invention will now be further described with reference to FIG. 9.

Figure 9:
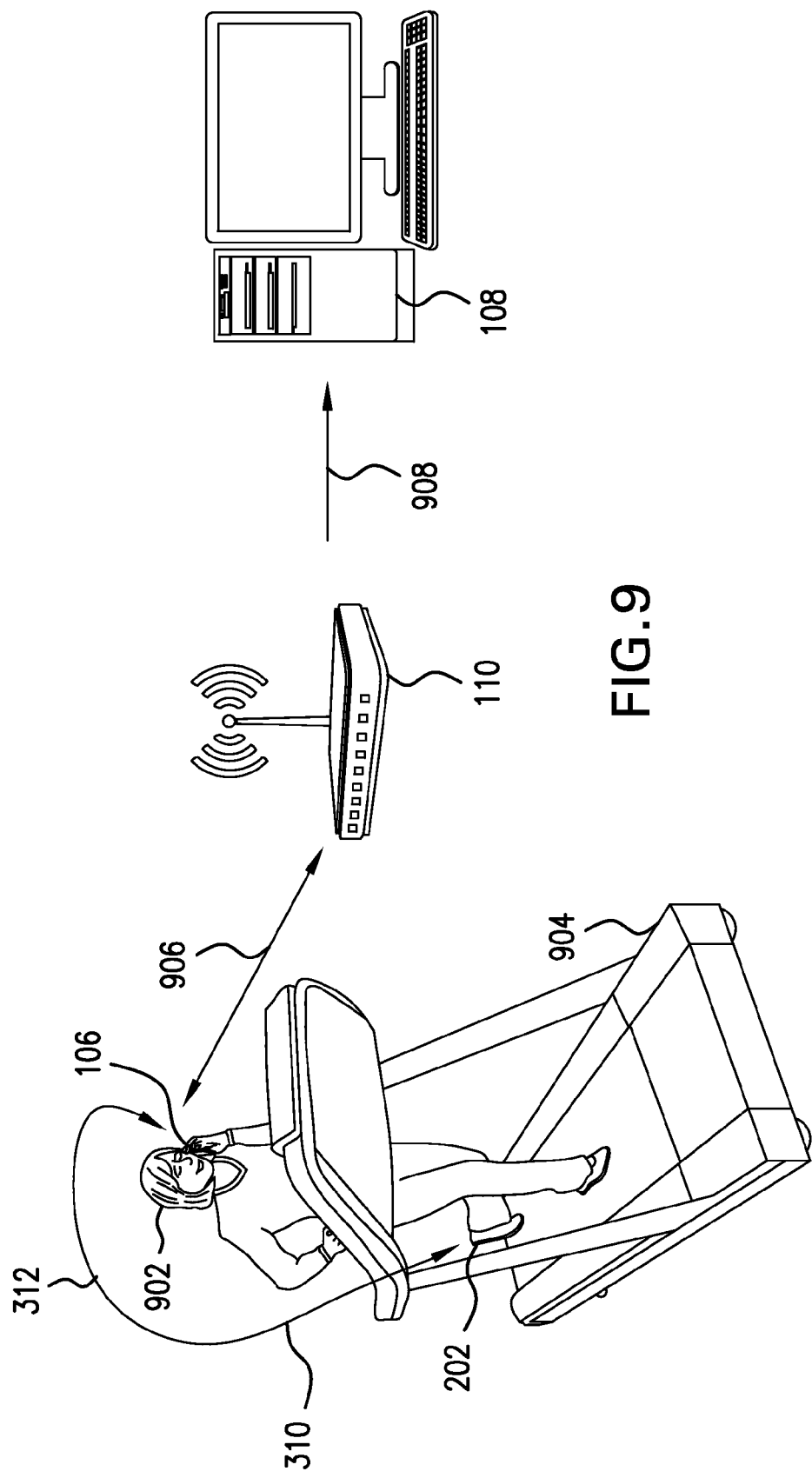
FIG. 9 illustrates uploading and downloading data between multiple electronic devices in accordance with aspects of the present invention.

As shown, FIG. 9 includes a user 902 wearing shoe 202, cell phone 106, a piece of exercise equipment 904, wireless router 110 and computer 108. In this example, shoe 202 is operable to output transmitted signal 312 to wireless router 110, which in turn will transmit the transmitted signal 312 to computer 108.

In the embodiment of FIG. 9, wireless device 204 of shoe 202 may download data via received signal 310 in a manner similar to that as discussed above with reference to FIG. 6. However, as opposed to receiving the downloaded data from wireless router 110, in this embodiment, cell phone 106 is an intermediary transceiver, wherein wireless device 204 downloads the data from cell phone 106.

Further, in the embodiment of FIG. 9, wireless device 204 of shoe 202 may upload data via transmitted signal 312 in a manner similar to that as discussed above with reference to FIG. 8. In this example, the data to be uploaded is exercise data associated with user 902 exercising on exercise equipment 904. However, as opposed to uploading data to wireless router 110, in this embodiment, cell phone 106 is an intermediary transceiver, wherein wireless device 204 uploads the data to cell phone 106.

In conventional systems, one of the main concerns with wireless devices is their inefficiency to maintain a long lasting battery. When a wireless device has the capability to search for a wireless network, but cannot find one, the device will continue to operate even when it is not in use. A cellphone is a primary example of a device that will operate even when the user is not playing a game, texting, or surfing the web. If the user puts their phone in their pocket and walks into a building that has no service, the phone will actively search for a new signal until one is detected; therefore using up more of the battery. In order to prevent draining a device's battery when not in use, there needs to be a way for the device to know when to be active.

Aspects of the present invention are drawn to a device and method that can detect when to be operational. Aspects of the present invention may be implemented for any wearable device that is able to upload/download data, non-limiting examples of which include a shoe, wristwatch, bracelet, etc., that keeps track of calories, miles run, etc. To save power, the user would only want to download or search for an update in specific instances, such as walking into their house or when they put on the device. A benefit of the present invention is drawn to the device not constantly searching for downloads (or searching to upload) if the device is not in an appropriate place at an appropriate time. A parameter detector in the device detects a predetermined parameter associated with an appropriate place and an appropriate time. Once the predetermined parameter is detected, a wake-up signal will instruct the chip to download/or upload data. This saves power over the conventional systems.

In the drawings and specification, there have been disclosed embodiments of the invention and, although specific terms are employed, they are used in a generic and descriptive sense only and not for purposes of limitation, the scope of the invention being set forth in the following claims.

What is claimed as new and desired to be protected by Letters Patent of the United States is:

1. A device for use with a wireless transceiver configured to transmit a data file containing one or more processing updates, said device comprising:
   a communication apparatus configured to wirelessly communicate with said wireless transceiver, said communication apparatus configured to enter a sleep mode based at least in part on: (i) a determination that said device is outside of a predetermined distance range to a router apparatus, and (ii) a determination that a user of said device has ceased movement for a predetermined period of time;
   a processor configured to operate according to a set of pre-loaded instructions;
   a sensor configured to detect a first parameter and to generate a parameter signal based on said detected first parameter; and
   a controller configured to generate a wake-up signal based on said parameter signal;
   wherein said communication apparatus is further configured to receive said data file containing said one or more processing updates when said wake-up signal is generated;
   wherein said processor is further configured to implement said one or more processing updates contained in said data file to alter operation thereof according to said one or more processing updates; and
   wherein said communication apparatus, said processor, said sensor and said controller comprise a unitary apparatus disposed at a shoe.

2. The device of claim 1, wherein said one or more processing updates comprise firmware updates; and
   wherein said receipt of said data file containing said one or more firmware updates occurs upon exiting said sleep mode via said wake-up signal.

3. The device of claim 1, further comprising one or more second sensors configured to collect sensed data while said communication apparatus is in said sleep mode; and said processor is further configured to process said sensed data via said set of pre-loaded instructions.

4. The device of claim 1, further comprising one or more second sensors configured to collect sensed data; and said processor is further configured to process said sensed data via said processing updates.

5. The device of claim 1, wherein said communication apparatus is further configured to request said processing update via a message sent to said router immediately upon exiting said sleep mode.

6. The device of claim 1, wherein said detection of said first parameter comprises detection that said devices is within said predetermined range of said router, and that said user of said device has resumed a threshold level of movement.

7. The device of claim 1, further comprising one or more second sensors configured to collect sensed data; and wherein said implementation of said one or more processing updates comprises said processor configured to process said sensed data via said one or more processing updates.

8. A method of using a wireless transceiver configured to receive a processing update at a shoe apparatus, said method comprising:
   causing a communication apparatus of said shoe apparatus to enter a sleep mode based at least in part on: (i) a determination that said shoe apparatus is outside of a predetermined distance range to a router apparatus, and (ii) a determination that a user of said shoe apparatus has ceased movement for a predetermined period of time;
   detecting, via a parameter detecting component of said shoe apparatus, a first parameter;
   generating, via said parameter detecting component of said shoe apparatus, a parameter signal based on said detected first parameter;
   generating, via a controlling component of said shoe apparatus, a wake-up signal based on said parameter signal;

wirelessly receiving, via said communication component of said shoe apparatus, said processing update when said wake-up signal is generated; and altering operation of a processing component of said shoe apparatus from a first pre-programmed manner to a second updated manner according to said processing update.

9. The method of claim 8, further comprising in response to said act of generating said wake-up signal, causing at least one of said processing component and said communication component to awaken from said sleep mode; and wherein said processing update comprises a firmware update.

10. The method of claim 8, further comprising:

continuing to collect sensed data via one or more second sensors of said shoe apparatus while said communication apparatus is in said sleep mode; and processing said sensed data using a set of previously loaded instructions at said processor of said wireless device.

11. The method of claim 8, further comprising:

collecting sensed data via one or more second sensors of said shoe apparatus; and processing said sensed data using said updated set of instructions transmitted via said processing update.

12. The method of claim 8, wherein said act of detecting said first parameter comprises detecting: (i) that said shoe apparatus is within said predetermined range of said router, and (ii) that said user of said shoe apparatus has resumed a threshold level of movement.

13. The method of claim 8, wherein said altering operation of a processing component of said shoe apparatus comprises:

collecting sensed data via one or more second sensors of said shoe apparatus; and processing said sensed data using said updated set of instructions transmitted via said processing update.

14. A method for receiving a processing update to a wireless device housed within a shoe, said method comprising:

operating a processor of said wireless device housed within said shoe according to a set of pre-loaded instructions;

causing a transceiver of said wireless device housed within said shoe to enter a sleep mode based at least in part on: (i) a determination that said wireless device is outside of a predetermined distance range to a router apparatus, and (ii) a determination that a user of said wireless device has ceased movement for a predetermined period of time;

in response to a detection by one or more sensors of said wireless device housed within said shoe of a first parameter, causing said transceiver of said wireless device to exit said sleep mode via a wake-up signal;

upon exiting said sleep mode via said wake-up signal, receiving said processing update at said transceiver of said wireless device housed within said shoe; and causing said processor of said wireless device housed within said shoe to be reprogrammed according to an updated set of instructions transmitted via said processing update.

15. The method of claim 14, further comprising continuing to collect sensed data via one or more second sensors of said wireless device while said transceiver is in said sleep mode.

16. The method of claim 15, further comprising processing said sensed data collected while said transceiver is in said sleep mode using said set of pre-loaded instructions at said processor of said wireless device.

17. The method of claim 14, wherein said act of receiving said processing update at said transceiver of said wireless device further comprises causing said transceiver apparatus to request said processing update via a message sent to a router upon exiting said sleep mode.

18. The method of claim 14, wherein said act of reprogramming said processor comprises:

collecting sensed data via one or more second sensors of said wireless device; and processing said sensed data using said updated set of instructions transmitted via said processing update.

19. The method of claim 14, wherein said processing update comprises a firmware update.

20. The method of claim 14, wherein said detection of said first parameter comprises detecting: (i) that said wireless device is within said predetermined range of said router, and (ii) that said user of said wireless device has resumed a threshold level of movement.

* * * * *